United States Patent [19]
Vanderlaan et al.

[11] Patent Number: 6,087,415
[45] Date of Patent: Jul. 11, 2000

[54] BIOMEDICAL DEVICES WITH HYDROPHILIC COATINGS

[75] Inventors: Douglas G. Vanderlaan; David C. Turner; Joe M. Wood, all of Jacksonville, Fla.

[73] Assignee: Johnson & Johnson Vision Care, Inc., Jacksonville, Fla.

[21] Appl. No.: 09/096,148

[22] Filed: Jun. 11, 1998

[51] Int. Cl.[7] .............................. A61F 2/00; C08L 33/02
[52] U.S. Cl. ...................... 523/105; 523/106; 523/107; 427/2.24; 424/422; 424/450; 604/264
[58] Field of Search ..................................... 523/106, 107, 523/105; 427/2.24; 604/264; 424/422, 450

[56] References Cited

U.S. PATENT DOCUMENTS

| | | |
|---|---|---|
| 4,293,642 | 10/1981 | Beavan et al. . |
| 4,521,564 | 6/1985 | Solomon et al. . |
| 4,546,123 | 10/1985 | Schafer et al. . |
| 4,876,126 | 10/1989 | Takemura et al. . |
| 4,973,493 | 11/1990 | Guire . |
| 5,002,582 | 3/1991 | Guire ........................................ 427/2.24 |
| 5,263,992 | 11/1993 | Guire . |
| 5,350,800 | 9/1994 | Verhoeven et al. . |
| 5,409,731 | 4/1995 | Nakagawa et al. . |
| 5,578,675 | 11/1996 | Mormile et al. . |
| 5,584,882 | 12/1996 | Yabushita et al. . |
| 5,670,558 | 9/1997 | Onishi et al. . |

FOREIGN PATENT DOCUMENTS

| | | |
|---|---|---|
| WO 89/09246 | 10/1989 | WIPO . |
| WO 91/04283 | 4/1991 | WIPO . |
| WO 93/00391 | 7/1993 | WIPO . |

*Primary Examiner*—Andrew E. C. Merriam
*Attorney, Agent, or Firm*—Lois A. Gianneschi

[57] ABSTRACT

Biomedical devices with stable, hydrophilic and antimicrobial coatings are provided. The coatings are formed using a coupling agent to bond a carboxyl containing hydrophilic coating to the surface by ester or amide linkages.

22 Claims, No Drawings

BIOMEDICAL DEVICES WITH HYDROPHILIC COATINGS

FIELD OF THE INVENTION

This invention relates to coated devices. In particular, the invention provides biomedical devices on the surfaces of which stable, hydrophilic, antimicrobial coatings are formed via coupling of the coating to the surface by ester or amide linkages.

BACKGROUND OF THE INVENTION

Devices for use in and on the human body are well known. The chemical composition of the surfaces of such devices plays a pivotal role in dictating the overall efficacy of the devices. For example, many devices, including catheters, stents, lenses, and implants require biologically non-fouling surfaces, meaning that proteins, lipids, and cells will not adhere to the surface. Lenses also must be wettable by tear fluid in order to ensure wearer comfort. Additionally, providing such devices with an antimicrobial surface is advantageous.

A wide variety of methods have been developed to coat device surfaces to provide them with desired characteristics. However, the need still exists for a simple, efficient process that will provide a stable, hydrophilic, antimicrobial coating.

DETAILED DESCRIPTION OF THE INVENTION AND PREFERRED EMBODIMENTS

The present invention provides a simple, economical process for producing devices with stable surface coatings, which coatings are both hydrophilic and antimicrobial. By "antimicrobial" is meant that bacterial adherence to the device surface is reduced in comparison to the uncoated surface, by about 30 percent or more.

In one embodiment, the invention provides a method for manufacturing biomedical devices comprising, consisting essentially of, and consisting of contacting at least one surface of a biomedical device with a coating effective amount of a carboxyl-functional polymer and a coupling effective amount of at least one coupling agent to produce a stable, hydrophilic and antimicrobial coating on the surface. In another embodiment, the invention provides biomedical devices comprising, consisting essentially of, and consisting of a biomedical device at least one surface of the device having a carboxyl functional polymer coating coupled thereto by at least one coupling agent.

By "biomedical device" is meant any device designed to be used while in or on either or both human tissue or fluid. Examples of such devices include, without limitation, stents, implants, catheters, and ophthalmic lenses. In a preferred embodiment, the biomedical device is an ophthalmic lens including, without limitation, contact or intraocular lenses. More preferably, the device is a contact lens.

It is an unexpected discovery of the invention that carboxyl functional polymers may be used to provide a stable, antimicrobial as well as hydrophilic coating for biomedical devices. By "stable" is meant that subjecting the coating to autoclaving, washing with a cleaning agent, and/or rinsing with a saline solution does not substantially alter the chemical properties of the coating. The coatings of the invention may be coupled to the device surface via ester linkages, amide linkages, or a combination thereof using certain coupling agents.

Coupling agents useful in the invention include, without limitation, carbodiimides, N,N'-carbonyldiimidazole, phosphoryl chloride, titanium tetrachloride, sulfuryl chloride fluoride, chlorosulfonyl isocyanate, phosphorus iodide, pyridinium salts of tributyl amine, phenyl dichlorophosphate, polyphosphate ester, chlorosilanes, and the like as well as mixtures of tributyl phosphorus and phenyl isocyanate, alkyl chloroformates and triethyl amine, 2-chloro-1,3,5-trinitrobenzene and pyridine, methyl sulfuryl chloride and diethyl amine, and triphenylphosphine, carbon tetrachloride and triethyl amine. Preferred coupling agents are carbodiimides. More preferred are 1-ethyl-3-(3-dimethylaminopropyl) carbodiimide and dicyclohexyl carbodiimide.

Although any number of polymers, such as those containing primary or secondary amino groups, hydroxyl groups, carboxyl groups, or mixtures thereof, may be useful in providing a hydrophilic coating, it has been discovered that the use of a carboxyl functional hydrophilic polymer, preferably poly(acrylic acid), provides a coating that is superior in hydrophilicity when compared to other such coatings. Further, these coatings provide the additional advantage of being antimicrobial.

Examples of suitable carboxyl functional hydrophilic polymers include, without limitation, poly(acrylic acid), poly(methacrylic acid), poly(maleic acid), poly(itaconic acid), block or random copolymers of (meth)acrylic acid, acrylic acid, maleic acid, itaconic acid with any reactive vinyl monomer, and the like, and mixtures thereof. Preferably, the carboxyl functional hydrophilic polymer is poly(acrylic acid) or poly(methacrylic acid). More preferably, poly(acrylic acid) is used.

The carboxyl functional polymers may be of any molecular weight. Preferably, the polymers are of a relatively high molecular weight, or about 10,0000 to 10,000,000, more preferably about 100,000 to about 4,000,000 g/mole, most preferably about 100,000 to about 1,000,000 g/mole.

One or more surfaces of a device may be coated using the process of the invention. Suitable surfaces for use in the invention are any surfaces with hydroxyl groups, amino groups, or mixtures thereof. Preferably, the surface is made of a silicone elastomer, hydrogel, or silicone-containing hydrogel. More preferably, the surface is a siloxane including, without limitation, polydimethyl siloxane macromers, methacryloxypropyl polyalkyl siloxanes, and mixtures thereof, silicone hydrogel or a hydrogel, such as etafilcon.

In the processes and devices of the invention, if the surface material to be coated does not contain the requisite functional group, such groups may be incorporated into the surface material. For example, hydroxyl groups may be incorporated by addition of one or more hydroxyl-containing monomers into the polymers used to form the surface. Examples of such hydroxyl containing monomers include, without limitation, mono(meth)acrylates of ethylene glycol, propylene glycol, glycerol, tetraethylene glycol, and the like. Amino groups may be incorporated using, without limitation, (meth)acrylates of aminoalcohols such as aminoethanol, tert-butylaminoethanol, or (meth) acrylamides of diamines such as bisaminopropane.

Alternatively, amine or hydroxyl functional, silicone-containing monomers or macromers may be used to incorporate the hydroxyl or amino functionalities into the surface. Suitable hydroxyl containing macromers include, without limitation, silicone containing linear or branched hydroxyalkylamine functional monomers of the structure:

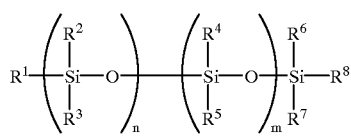

$$\text{I}$$

wherein: n is 0 to 500, m is 0 to 500, and n+m=10 to 500, preferably 20 to 250; $R^2$, $R^4$, $R^5$, $R^6$, and $R^7$ are each independently a substituted or, preferably, unsubstituted monovalent alkyl of 1 to 10 carbon atoms or a substituted or, preferably, unsubstituted aryl group, suitable substituents for which include alcohol, ester, amine, ketone, carboxylic acid, or ether groups; $R^1$, $R^3$, and $R^8$ are each independently a substituted or, preferably unsubstituted monovalent alkyl of 1 to 30 carbon atoms or a substituted or, preferably, unsubstituted aryl group suitable substituents for which are alcohol, ester, amine, ketone, carboxylic acid, or ether groups, and at least one of $R^1$, $R^3$, and $R^8$ is of the formula:

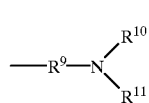

$$\text{II}$$

wherein $R^9$ is any group capable of linking N to Si, including without limitation, a linear or branched divalent alkyl of 1 to about 10 carbon atoms or an ether group, $R^{10}$ and $R^{11}$ are each independently H, a substituted or unsubstituted monovalent alkyl of 1 to 5 carbon atoms, a substituted or unsubstituted aryl group, suitable substituents for which are substituted with alcohol, ester, amine, ketone, carboxylic acid, or ether groups, or the structure:

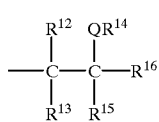

$$\text{III}$$

wherein $R^{14}$ is H or a monovalent (meth)acryloyl, styryl, vinyl, allyl, or N-vinyl lactam polymerizable group and preferably H or methacryloyl; $R^{16}$ is H, a monovalent substituted or unsubstituted alkyl group of 1 to 6 carbon atoms, a substituted or unsubstituted aryl group, suitable substituents for which are alcohol, ester, amine, ketone, carboxylic acid, or ether groups, or a (meth)acrylate, styryl, vinyl, allyl, or N-vinyl lactam polymerizable group and preferably is an alkyl group of 1 to 6 carbon atoms substituted with an alcohol or is a methacrylate; $R^{12}$, $R^{13}$, and $R^{15}$ are independently H, a substituted or unsubstituted monovalent alkyl of 1 to 6 carbon atoms, a substituted or unsubstituted aryl, suitable substituents for which include alcohol, ester, amine, ketone, carboxylic acid, or ether groups, or $R^{12}$ and $R^{15}$ or $R^{13}$ and $R^{15}$ form a ring structure with the proviso that at least some of the structure II groups on the monomer are polymerizable groups. Preferably, $R^{12}$, $R^{13}$, and $R^{15}$ are H.

Silicone-containing polymers useful in the present invention may also be copolymers incorporating one or more hydrophilic monomers. The hydrophilic monomers used to make the hydrogel used in the invention may be any of the known monomers useful for hydrogel formation.

Preferred hydrophilic monomers used in forming the surfaces coated by the process of this invention are acrylic or vinylic-containing. Acrylic-containing monomers contain the group ($CH_2=CRCOX$) wherein R is H or $CH_3$, and X is O or N. Examples of such monomers include, without limitation, N,N-dimethyl acrylamide, 2-hydroxyethyl methacrylate, glycerol methacrylate, 2-hydroxy ethyl methacrylamide, polyethylene glycol monomethacrylate, methacrylic acid, acrylic acid, and the like.

Vinylic-containing monomers refers to monomers containing the group (—CH=$CH_2$). Examples of such monomers include, without limitation, N-vinyl lactams, such as N-vinyl pyrrolidone, and N-vinyl-N-methyl acetamide, N-vinyl-N-ethyl acetamide, N-vinyl-N-ethyl formamide, N-vinyl formamide and the like. Preferably, the monomer is N-vinyl pyrrolidone.

Other hydrophilic monomers that may be employed in forming the surfaces of the invention include, without limitation, polyoxyethylene polyols having one or more terminal hydroxyl groups replaced with a functional group containing a polymerizable double bond. Examples include, without limitation, polyethylene glycol, ethoxylated alkyl glucoside, and ethoxylated bisphenol A reacted with one or more equivalents of an end-capping group such as isocyanatoethyl methacrylate, methacrylic anhydride, methacryloyl chloride, vinylbenzyloyl chloride, or the like to produce a polyethylene polyol having one or more terminal, polymerizable, olefinic groups bonded to the polyethylene polyol through linking moieties such as carbamate or ester groups.

Additional exemplary hydrophilic monomers are disclosed in U.S. Pat. Nos. 5,070,215 and 4,910,277, which are incorporated herein in their entireties by reference. Preferred hydrophilic monomers are N,N-dimethyl acrylamide, 2-hydroxyethyl methacrylate, glycerol methacrylate, 2-hydroxyethyl methacrylamide, N-vinyl pyrrolidone, polyethylene glycol monomethacrylate, and (meth)acrylic acid. Most preferably, N,N-dimethyl acrylamide is used.

In the process of the invention, the surface to be coated is contacted with the polymer and at least one coupling agent in any convenient manner. For example, the device may be placed in a solution of polymer and solvent into which the coupling agent is added. As an alternative, the polymer or the device surface may first be treated with the coupling agent and the surface then placed in a polymer solution.

Suitable solvents for use in the invention are those that are capable of solubulizing both the carboxyl-functional polymer and the coupling agent. Preferably, the coating process is carried out in a water or aqueous solution, which solution preferably contains buffers and salts. The carbodiimide 1-ethyl-3-(3-dimethylaminopropyl)carbodiimide ("EDC") is effective in aqueous solutions and, thus, is a most preferred coupling agent.

The coupling agents may be used alone or in combination with agents capable of stabilizing any reactive intermediate formed. For example, EDC may be used with N-hydroxysuccinimide as a stabilizer. Additionally, it may be necessary to adjust the solution pH in order to optimize ester or amide linkage formation. Preferably, the pH is adjusted to from about 2.0 to about 8.0, more preferably from about 4.5 to about 5.0.

A coupling effective amount of the coupling agent is used which amount is sufficient to couple the polymer to the device surface. The precise amount of coupling agent used will depend on the surface's chemistry as well as the polymer and coupling agent selected. Generally, about 0.01 to about 10 weight percent, preferably about 0.01 to about 5.0, more preferably, about 0.01 to about 1 weight percent of the coating solution is used. By coating solution is meant the polymer with one or more of the solvent, coupling agent, and buffer. Typically, the amount of coating solution used per lens will be about 0.1 to about 100 g, preferably about 0.5 to about 50 grams, more preferably about 1 to about 10 g per lens.

A coating effective amount of polymer is used meaning an amount sufficient to coat the surface to the desired degree. Generally, the amount of polymer used is about 0.001 to about 100, preferably about 0.01 to about 50, more preferably, about 0.01 to about 10 weight percent of the coating solution.

Temperature and pressure are not critical to the process of the invention and the process may be conveniently carried out at room temperature and pressure. However, in a preferred embodiment, a temperature of about 30 to about 60° C. is used. The contact time used will be a length of time sufficient to coat the surface to the extent desired. If the surface is being contacted with a coupling agent-polymer solution, generally, contact times will be from about 1 minute to about 24 hours, preferably from about 1 to about 120 minutes, more preferably from about 1 minute to about 60 minutes.

If the surface is first treated with only the coupling agent, the contacting time will be about 1 to about 120, preferably 2 to about 60 minutes. The surface then is contacted with the polymer-solvent solution as described above.

Following contacting, the surface may be washed with water or buffered saline solution to remove unreacted polymer, coupling agent, solvent, and byproducts. Optionally, the coated surface may be heated in water to extract residual coating, coupling agent, and byproducts and to ensure the break down of any coupling agent-stabilizer complexes that may have formed.

In one embodiment of the invention, after coating with the carboxyl functional polymer, the coated surface may be further modified. For example, the coated surface may be reacted with monomers or polymers capable of reacting with the functional groups of the coating. Such further reaction may be conducted using any suitable coupling agent, including those disclosed hereinabove. Illustrative useful monomers include, without limitation, alcohols, such as methanol and ethanol, polyols such as ethylene glycol and glycerol, amines such as n-butylamine, methylamine, ammonia, ethanolamine or diethanol amine, and the like. However, one ordinarily skilled in the art will recognize that the selection of the modifying monomer or polymer will depend on the modification desired to be imparted to the coated surface.

One ordinarily skilled in the art will recognize that the formulation for producing the surface to be coated by the method of the invention may contain other monomers and additives. For example, ultra-violet absorbing monomers, reactive tints, processing aids, and the like may be used.

The invention will be further clarified by a consideration of the following, non-limiting examples.

EXAMPLES

Preparation 1

Silicone-containing contact lenses were prepared according to the following procedure. 500 g of α,ω-bisaminopropyl polydimethylsiloxane (5000 MW) and 68 g of glycidyl methacrylate were combined and heated with stirring at 100° C. for 10 hours. The product was extracted five times with 1500 ml of acetonitrile to remove residual glycidyl methacrylate to give a clear oil. Infra-red spectra were as follows: 3441 $cm^{-1}$, 2962 $cm^{-1}$, 1944 $cm^{-1}$, 1725 $cm^{-1}$, 1638 $cm^{-1}$, 1612 $cm^{-1}$, 1412 $cm^{-1}$.

A blend of 25.35 wt percent of his reaction product, 25.35 wt percent 3-methacryloxypropylbis(trimethylsiloxy) methylsilane ("MBM"), 27.3 wt percent N,N-dimethylacrylamide ("DMA"), 0.31 wt percent 2-hydroxy-2-methyl-1-phenyl-propan-1-one available as DAROCUR™ 1173, 13.2 wt percent 3-methyl-3-pentanol, and 8.8 wt percent octamethylcyclotetrasiloxane was cured in a contact lens molds using UV light. The molds were opened and lenses released into isopropanol and then transferred into a borate-buffered solution.

Example 1

170 of the Preparation 1 lenses were immersed in 313 g of a borate-buffered saline solution containing 1.5 wt percent (250,000 MW) poly(acrylic acid). 0.62 g EDC were added and the mixture was agitated at room temperature for 1 hour. The lenses were then rinsed five times with fresh saline solution. The dynamic contact angles with borate-buffered saline were measured using a Wilhelmy balance before and after coating. The results are shown on Table 1.

The coated lenses were autoclaved five times at 121° C. and the dynamic contact angles measured. The results are shown on Table 1.

Several of the autoclaved lenses were cleaned using a digital rub and a cleaner of purified water, isopropyl alcohol (15.7 percent w/w), poloxamer 407, and amphoteric 10 (available as MIRAFLOW™). The lenses were rinsed with saline and the dynamic contact angles of the autoclaved and cleaned lenses were measured with borate-buffered saline before and after coating. The results are shown on Table 1.

Comparative Example 1

Five Preparation 1 lenses were immersed in a borate-buffered saline solution containing 1.5 wt percent (250,000 MW) poly(acrylic acid) as in Example 1, except that no EDC was added. The mixture was agitated at room temperature for 1 hour and then the lenses were rinsed five times with fresh saline solution. One lens was cleaned using a digital rub and MIRAFLOW™. The lens was rinsed with saline and was unwettable.

Preparation 2

2.48 g 1,3-bis(3-aminopropyl)-tetramethyldisiloxane, 83.62 g octamethylcyclotetrasiloxane, 13.37 g 3-aminopropylmethyldiethoxysilane, 0.1 g potassium hydroxide, and 10.0 g water were combined and heated to 145° C., with stirring and removal of a water and ethanol azeotrope. The mixture was cooled to 60° C. and 0.13 g acetic acid added. The mixture was stirred for 1 hour and filtered through celite. The product was devolatilized by heating to 145° C. at about 1 torr.

10 g of the aminofunctional polysiloxane fluid produced were combined with 1.33 g glycidol and 0.729 g glycidyl methacrylate. A moderate exotherm was noted. The mixture was allowed to react for three days during which time it became very viscous. The product was a pendant hydroxyalkylamine-functional, silicone-containing monomer.

12.06 parts of the monomer were copolymerized with 7.24 g DMA, 4.82 methacryloxypropyltris(trimethylsiloxy) silane ("TRIS"), and 0.06 g DAROCURE™ 1173 by exposure to UV light in a contact lens mold. The resulting lenses were soaked in isopropyl alcohol to remove any residual monomers and then equilibrated in borate-buffered solution.

Example 2

25 lenses from Preparation 2 were immersed in 46.46 g borate-buffered saline to which 1.95 g of a 35 wt percent aqueous solution of poly(acrylic acid) (250,000 MW) had been added. 0.09 g EDC were added and the mixture agitated at room temperature for 5 minutes. The lenses were then rinsed 4 times with fresh saline solution and the dynamic contact angles were measured as in Example 1. The results are shown on Table 1.

Example 3

30 Preparation 1 lenses were immersed in 29.3 g of a 1.0% solution of EDC in borate buffered saline at room temperature for one hour. The lenses were transferred into 132 g of a solution of 3.0% (250,000 MW) poly(acrylic acid) in borate buffered saline. After one hour at room temperature, 0.38 g EDC were added. After one hour at room temperature, the lenses were rinsed with borate buffered saline. They were then placed into 60 g of 5% glycerol in borate buffered saline, to which 0.60 g EDC were added. After one hour at room temperature, the lenses were rinsed five times with fresh borate buffered saline solution. The lenses were found to be very wettable.

Preparation 3

Contact lenses were made by placing a blend of 15 wt percent 4,600 average molecular weight polyethylene glycol dimethacrylate, 2.0 wt percent 1,3-bis(3-methacryloxypropyl)tetrakis(trimethylsiloxy)disiloxane, 30 wt percent 350 average molecular weight methoxy polyethylene glycol methacrylate, 30.18 wt percent TRIS, 15 wt percent 3-(perfluoro-5-methylhexyl)-2-hydroxypropyl methacrylate, 3.0 wt percent methacrylic acid, 0.80 wt percent IRGACURE™ 1850, 4.0 wt percent NORBLOC™ 7966, and 0.02 wt percent of the 2-hydroxyethyl methacrylate adduct of Reactive Blue 2 blended with a diluent of polypropylene glycol (average of 20 repeating units) ethylhexyl alcohol (1:1 by wt with a reactive monomer to diluent ratio of 60:40 by wt) into lens molds and irradiating the molds with visible light. The resulting lenses were soaked in isopropyl alcohol to remove any residual monomers and then equilibrated in borate-buffered solution.

Example 4

20 Preparation 3 lenses were immersed in 40 ml of a borate-buffered saline solution containing 0.8 wt percent poly(acrylic acid) (250,000 MW). 0.06 g EDC were added and the mixture agitated at room temperature for 1 hr. The lenses were then rinsed repeatedly with deionized water. Dynamic contact angles were measured as for Example 1 and the results are shown on Table 1.

Preparation 4

Lenses were prepared as in Preparation 3 except that 2.0 wt percent of 2-hydroxyethylmethacrylate and 13 wt percent 3-(perfluoro-5-methylhexyl)-2-hydroxypropyl methacrylate were used.

Example 5

50 Preparation 4 lenses were immersed in 100 ml of borate-buffered saline solution containing 0.88 wt percent poly(acrylic acid), 250,000 MW. 0.15 g EDC were added and the mixture agitated at room temperature for 1 hr. The lenses were then rinsed repeatedly with borate-buffered saline. The lenses were found to be very wettable.

Preparation 5

12.5 g KOH were added to 350 g of 20 mole propoxylate of methyl glucose, available from Americol Corp., Edison, N.J. as GLUCAM™ P-20, in a high temperature/pressure reactor. The mixture was heated to 105° C. and stirred for 30 minutes with nitrogen sparging, and then pulling vacuum. After repeating the sparge/vacuum two more times, the pressure was allowed to rise to 10 psi and the temperature increased to 125° C. 1922 g propylene oxide were added gradually over 7 hours while maintaining a pressure of 30–40 psi and a temperature of 135° C. After continuing agitation overnight, 947 g ethylene oxide were added following a similar procedure. The product was neutralized with 9.1 g phosphoric acid and filtered with dicalite to give a slightly hazy liquid with a hydroxyl number of 28.3 mg KOH/g To a solution of 200 g of this product, 21.0 g triethylamine and 342 mg N,N-dimethylaminopyridine in 600 g dry ethylene glycol dimethyl at 40° C. were added 32.1 g of methacrylic anhydride in 250 g ethylene glycol dimethyl ether dropwise to the reaction flask over a 7 to 8 hour period. The reaction was continued at 40° C. for 7 days.

The reaction temperature was decreased to 25° C. and 100 ml deionized water were added. The pH of the reaction mixture was adjusted to 7.0 using a 5% aqueous hydrochloric acid solution. 600 g of AMBERLITE™ IRA 96 were added and the mixture stirred for one and one half hours. The AMBERLITE™ IRA 96 was removed by filtration and the mixture volatilized at 30 to 35° C. under reduced pressure. Approximately 1 L chloroform was added and the resulting liquid was washed with an equal volume of 5% aqueous solution of sodium bicarbonate twice and with saturated sodium chloride once. The organic layer was passed through a 400 g silica bed. 100 mg of 4-methoxyphenol were added and the chloroform removed under pressure. Approximately 75 ml methanol were added and then removed under reduced pressure to remove residual chloroform and yield a macromer.

A blend was made of 11.2% of the macromer of Preparation 5, 40% TRIS, 28% DMA, 0.8% DAROCUR™ 1173, and 20% 1-hexanol. The blend was cured in contact lens molds by exposure to UV light for 30 minutes. The molds were opened and the lenses released into a blend of isopropanol and water, rinsed with isopropanol, and placed in borate-buffered saline.

Example 6

35 Preparation 5 lenses were immersed in 184 ml of a borate-buffered saline solution containing 1.37 wt percent poly(acrylic acid) (250,000 MW). 0.030 g EDC were added and the mixture agitated at room temperature for 1 hr. The lenses were then rinsed repeatedly with a borate-buffered saline solution and the contact angles measured. The results are shown on Table 1.

Preparation 6

3.26 g of the macromer of Preparation 5 were combined with 12.5 TRIS, 8.78 g DMA, 0.27 g DAROCUR™ 1173, 0.96 g 2-hydroxyethyl methacrylate, 0.0078 g of the adduct of 2-hydroxyethyl methacrylate and Reactive Blue 2 and 5.03 g 1-hexanol. This blend was cured in contact lens molds by exposure to UV light for 30 minutes. The molds were opened and the lenses released into a blend of isopropanol and water, rinsed with isopropanol, and placed in borate-buffered saline.

Example 7

35 Preparation 6 lenses were immersed in 184 ml of a borate-buffered saline solution containing 1.37 wt percent poly(acrylic acid) (250,000 MW). 0.03 g EDC were added and the mixture agitated at room temperature for 1 hour. The lenses were then rinsed repeatedly with a borate-buffered saline solution and the contact angles measured. The results are shown on Table 1.

Example 8

35 ETAFILCON™ lenses were immersed in 184 ml of a borate-buffered saline solution containing 1.37 wt percent poly(acrylic acid) (250,000 MW). 0.030 g EDC were added and the mixture agitated at room temperature for 1 hr. The lenses were then rinsed repeatedly with a borate-buffered saline solution and the contact angles measured. The resulting lenses were very wettable and lubricious.

Example 9

Two lenses from Preparation 1 were placed in a solution of 10% EDC and 0.25% poly(acrylic acid) (750,000 MW) at room temperature. After 20 minutes. The lenses were removed and rinsed with borate-buffered saline solution. The lenses were wettable.

TABLE 1

| Example | Uncoated Lens Advance Angle (°) | Coated Lens Advance Angle (°) | Uncoated Lens Receding Angle (°) | Coated Lens Receding Angle (°) |
| --- | --- | --- | --- | --- |
| 1 | 135 | 45 | 62 | 40 |
| 1 (after autoclave) | — | 50 | — | 39 |
| 1 (after autoclave and cleaning) | — | 58 | — | 52 |
| 2 | 114 | 32 | 56 | 35 |
| 2 (after autoclave) | — | 35 | — | 45 |
| 2 (after autoclave and cleaning) | — | 35 | — | 39 |
| 4 | 148 | 50 | 50 | 44 |
| 4 (after autoclave) | — | 45 | — | 45 |
| 4 (after autoclave and cleaning) | — | 49 | — | 42 |
| 6 | 111 | 44 | 52 | 44 |
| 6 (after autoclave) | — | 55 | — | 50 |
| 6 (after autoclave and cleaning) | — | 71 | — | 55 |
| 7 | 111 | 46 | 52 | 49 |
| 7 (after autoclave) | — | 39 | — | 44 |
| 7 (after autoclave and cleaning | — | 52 | — | 50 |
| 8 | 76 | 58 | 48 | 54 |
| 8 (after autoclave) | — | 56 | — | 39 |
| 8 (after autoclave and cleaning) | — | 39 | — | 44 |

Examples 10 and 11

A culture of *pseudomonas aeruginosa*, ATCC # 15442 (from ATCC, Rockville, Md.) was grown overnight in 150 ml tryptic soy broth. A standardized phosphate buffered saline, PBS, washed bacterial inoculum was prepared containing $1\times10^8$ cfu/ml. The bacteria were applied to lenses from Examples 1 and 8, both coated and uncoated with poly(acrylic acid). The contact lenses were washed with PBS. Each washed lens was combined with 2 ml of the standardized bacterial inoculum in a glass vial, which vial was shaken at 100 rpm in a rotary shaker-incubator for 2 hr at 35° C. Each lens was washed with PBS, placed into 10 ml of PBS containing 0.05 percent TWEEN™ 80 and vortexed at 2000 rpm for 3 minutes at room temperature. The resulting supernatant was enumerated for viable bacteria. The results, reported on Table 2, show that the poly(acrylic acid) coating greatly reduced adhesion of bacteria to the lenses. The lenses were wettable.

TABLE 2

|  | Uncoated | Coated | Percent Reduction |
| --- | --- | --- | --- |
| Example 1 | $17.7 \times 10^6$ CFU | $0.20 \times 10^6$ CFU | 99% |
| Example 8 | $3.54 \times 10^6$ CFU | $0.051 \times 10^6$ CFU | 99% |

Example 12

Preparation 1 lenses are immersed in 313 g of a borate-buffered saline solution containing 1.5 wt percent (100,000 MW) poly(acrylic acid). 0.62 g EDC are added and the mixture was agitated at room temperature for 1 hour. The lenses are then rinsed five times with fresh saline solution.

Example 13

Lenses from Preparation 2 are immersed in 46.46 g borate-buffered saline to which 1.95 g of a 35 wt percent aqueous solution of poly(acrylic acid) (150,000 MW) are added. 0.09 g EDC are added and the mixture agitated at room temperature for 5 minutes. The lenses are then rinsed 4 times with fresh saline solution. The resulting lenses are wettable.

What is claimed is:

1. A device comprising a biomedical device at least one surface of the biomedical device comprising hydroxyl groups, amino groups, or mixtures thereof, the surface having a coating effective amount of a synthetic carboxyl functional polymer coupled thereto by a coupling effective amount of at least one coupling agent, wherein the coupling agent is selected from the group consisting of carbodiimides, N,N'-carbonyldiimidazole, phosphoryl chloride, titanium tetrachloride, sulfuryl chloride fluoride, chlorosulfonyl isocyanate, phosphorus iodide, pyridinium salts of tributyl amine, phenyl dichlorophosphate, polyphosphate ester, chlorosilanes, a mixture of tributyl phosphorus and phenyl isocyanate, a mixture of alkyl chloroformates and triethyl amine, a mixture of 2-chloro-1,3,5-trinitrobenzene and pyridine, a mixture of methyl sulfuryl chloride and diethyl amine, and a mixture of triphenylphosphine, carbon tetrachloride and triethyl amine.

2. The device of claim 1, wherein the biomedical device is a contact lens.

3. The device o f claim 1 wherein the surface comprises hydroxyl groups.

4. The device of claim 1 wherein the surface comprises amino groups.

5. The device of claim 1 wherein the synthetic carboxyl functional polymer is poly(acrylic acid), poly(methacrylic acid), poly(maleic acid), poly(itaconic acid), block or random copolymers of methacrylic acid, acrylic acid, maleic acid, or itaconic acid with a reactive vinyl monomer, or mixtures thereof.

6. The device of claim 5 wherein the carboxyl functional polymer is poly(acrylic acid).

7. The device of claim 1 wherein the coupling agent is a carbodiimide.

8. The device of claim 7 wherein the carbodiimide is 1-ethyl-3-(3-dimethylaminopropyl)carbodiimide.

9. A contact lens at least one surface of which comprises a polymer selected from the group consisting of silicone elastomer, hydrogel, and silicone-containing hydrogel, the polymer having functional groups selected from the group consisting of hydroxyl groups, amino groups, and mixtures thereof, the surface having a coating effective amount of a carboxyl-functional polymer coupled thereto by a coupling effective amount of a carbodiimide coupling agent, which carboxyl-functional polymer is selected from the group consisting of poly(acrylic acid), poly(methacrylic acid), poly(maleic acid), poly(itaconic acid), block or random copolymers of methacrylic acid, acrylic acid, maleic acid, or itaconic acid with a reactive vinyl monomer, and mixtures thereof.

10. The lens of claim 9 wherein the functional groups comprise hydroxyl groups.

11. The lens of claim 9 wherein the functional groups comprise amino groups.

12. The lens of claim 9 wherein the polymer comprises silicone elastomer.

13. The lens of claim 9 wherein the carboxyl functional polymer is polyacrylic acid.

14. The device of claim 9 wherein the carbodiimide is 1-ethyl-3-(3-dimethylaminopropyl)carbodiimide.

15. A contact lens at least one surface of which comprises a polymer selected from the group consisting of silicone elastomer, hydrogel, and silicone-containing hydrogel, the polymer having functional groups selected from the group consisting of hydroxyl groups, amino groups, and mixtures thereof, the at least one surface having a coating effective amount of poly(acrylic acid) coupled thereto by a coupling effective amount of a carbodiimide coupling agent.

16. The lens of claim 15 wherein the weight-average molecular weight of the poly(acrylic acid) is about 100,000 to about 1,000,000 g/mole.

17. The lens of claim 15 wherein the polymer comprises silicone elastomer.

18. The lens of claim 15 wherein the polymer comprises a hydrogel.

19. The lens of claim 15 wherein the polymer comprises a silicone containing hydrogel.

20. The device of claim 15 wherein the carbodiimide is 1-ethyl-3-(3-dimethylaminopropyl)carbodiimide.

21. The lens of claim 15 wherein the functional groups comprise hydroxyl groups.

22. The lens of claim 15 wherein the functional groups comprise amino groups.

* * * * *